Figure 1:
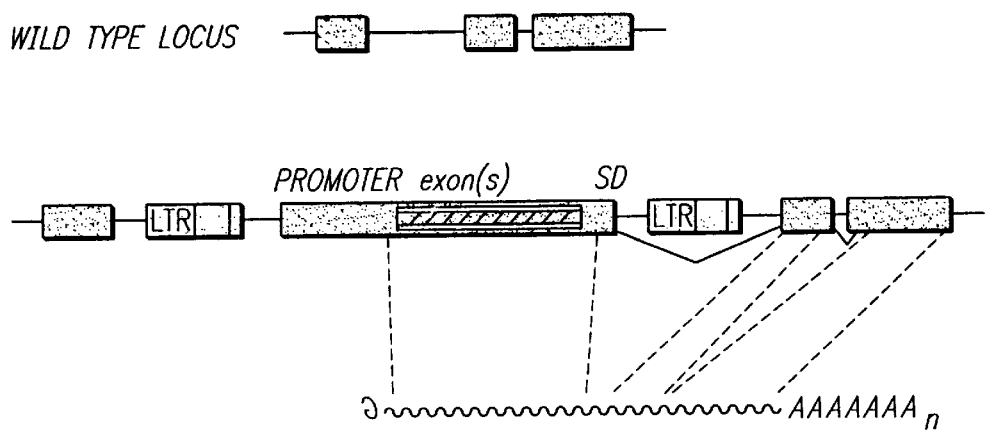

US006080576A

United States Patent [19]
Zambrowicz et al.

[11] Patent Number: 6,080,576
[45] Date of Patent: Jun. 27, 2000

[54] VECTORS FOR GENE TRAPPING AND GENE ACTIVATION

[75] Inventors: Brian Zambrowicz; Glenn Friedrich; Arthur T. Sands, all of The Woodlands, Tex.

[73] Assignee: Lexicon Genetics Incorporated, The Woodlands, Tex.

[21] Appl. No.: 09/057,328

[22] Filed: Apr. 8, 1998

Related U.S. Application Data

[60] Provisional application No. 60/079,729, Mar. 27, 1998.

[51] Int. Cl.$^7$ ............................ C12N 15/63; C12N 15/85; C12N 15/00
[52] U.S. Cl. ...................... 435/320.1; 435/325; 435/455; 435/463
[58] Field of Search ................................. 435/320.1, 325; 800/8, 13, 18

[56] References Cited

U.S. PATENT DOCUMENTS

| | | |
|---|---|---|
| 4,190,496 | 2/1980 | Rubenstein et al. . |
| 5,449,614 | 9/1995 | Danos et al. . |
| 5,464,764 | 11/1995 | Capecchi et al. . |
| 5,521,076 | 5/1996 | Mulligan et al. . |
| 5,625,048 | 4/1997 | Tsien et al. . |
| 5,733,761 | 3/1998 | Treco et al. . |

FOREIGN PATENT DOCUMENTS

| | | |
|---|---|---|
| WO 98/20031 | 5/1998 | WIPO . |
| WO 98/24918 | 6/1998 | WIPO . |

OTHER PUBLICATIONS

Campbell et al. (Jan. 1997) Theriogenology, vol. 47, 63–72.
Evans et al. (Sep. 1997) TIG, vol. 13 (9), 340–347.
Niwa et al. (1993) J. Biochem., vol. 113, 343–349.
Skarnes et al. (1993) Curr. Opin. Biotech., vol. 4, 684–689.
Yoshida et al., 1995, "A new strategy of gene trapping in ES cells using 3'RACE", *Transgenic Research* 4:277–287.
Campbell et al., 1997, "Totipotency or Multipotentiality of Cultured Cells: Applications and Progress", *Theriogenology* 47:63–72.
Chang et al., 1993, "Enrichment of Insertional Mutants Following Retrovirus Gene Trap Selection", *Virology* 193:737–747.
Evans et al., 1997, "Gene trapping and functional genomics", *TIG* 13(9):370–374.
Gogos et al., 1997, "Selection for Retroviral Insertions into Regulated Genes", *Journal of Virology* 71(2): 1644–1650.
Gogos et al., 1996, "Gene Trapping in Differentiating Cell Lines: Regulation of the Lysosomal Protease Cathepsin B in Skeletal Myoblast Growth and Fusion", *Journal of Cell Biology* 134(4):837–847.
Hicks et al., 1997, "Functional genomics in mice by tagged sequence mutagenesis", *Nature Genetics* 16:338–344.
Jönsson et al., 1996, "Use of a Promoter–Trap Retrovirus to Identify and Isolate Genes Involved in Differentiation of a Myeloid Progenitor Cell Line In Vitro", *Blood* 87(5): 1771–1779.

Niwa et al., 1993, "An Efficient Gene–Trap Method Using Poly A Trap Vectors and Characterization of gene–trap events", *J. Biochem 113(3):343–349*.
Skarnes, 1993, "The Identification of new genes: gene trapping in transgenic mice", *Current Opinion in Biotechnology* 4:684–689.
Zambrowicz et al., 1997, "Disruption of overlapping transcripts in the ROSA βgeo 26 gene trap strain leads to widespread expression of β–galactosidase in mouse embryos and hematopoietic cells", *Proc. Natl. Acad. Sci. USA* 94:3789–3794.
Cho et al., 1976, "Revertants of Human Cells Transformed by Murine Sarcoma Virus," *Science* 194:951–953.
Frohman, 1994, "On Beyond Classic RACE (Rapid Amplification of cDNA Ends)," *PCR Methods and Applications* 4:S40–S58.
Houghten et al., 1991, "Generation and use of synthetic peptide combinatorial libraries of basic research and drug discovery," *Nature* 354:84–86.
Inoue et al., 1983, "Rat Mutant Cells Showing Temperature Sensitivity for Transformation by Wild–Type Moloney Murine Sarcoma Virus," *Virology* 125:242–245.
Lam et al., 1991, "A new type of synthetic peptide library for identifying ligand–binding activity," *Nature* 354:82–84.
Maruyama et al., 1981, "Characterization of Flat Revertant Cells Isolated from Simian Virus 40–Transformed Mouse and Rat Cells Which Contain Multiple Copies of Viral Genomes," *J. Virol.* 37:1028–1043.
Mathey–Prevot et al., 1984, "Revertants and Partial Transformants of Rat Fibroblasts Infected with Fujinami Sarcoma Virus," *J. Virol.* 50:325–334.
Norton et al., 1984, "Expression of Kirsten Murine Sarcoma Virus in Transformed Nonproducer and Revertant NIH/3T3 Cells: Evidence for Cell–Mediated Resistance to a Viral Oncogene in Phenotypic Reversion," *J. Virol.* 50:439–444.
Pestov and Lau, 1994, "Genetic selection of growth–inhibitory sequences in mammalian cells," *Proc. Natl. Acad. Sci. U.S.A.* 91:12549–12553.
Ryan et al., 1985, "Isolation of a Simian Virus 40 T–Antigen–Positive, Transformation–Resistant Cell Line by Indirect Selection," *Mol. Cell. Biol.* 5:3577–3582.
Sacks et al., 1979, "Abelson Murine Leukemia Virus–Infected Cell Lines Defective in Transformation," *Virology* 97:231–240.
Selten et al., 1985, "Proviral activation of the putative oncogene Pim–1 in MuLV induced T–cell lymphomas," *EMBO Journal* 4(7):1793–1798.

(List continued on next page.)

*Primary Examiner*—Bruce R. Campell
*Assistant Examiner*—AnneMarie S. Beckerleg
*Attorney, Agent, or Firm*—Pennie & Edmonds LLP

[57] ABSTRACT

A novel 3' gene trap cassette is described that does not encode a marker conferring antibiotic resistance and can be used to efficiently trap and identify cellular genes. Vectors incorporating the presently 3' gene trap cassette find particular application in gene discovery, the production of transgenic cells and animals, and gene activation.

21 Claims, 1 Drawing Sheet

OTHER PUBLICATIONS

Songyang et al., 1993, "SH2 Domains Recognize Specific Phosphopeptide Sequences," *Cell* 72: 767–778.

Stephenson et al., 1973, "Characterization of Morphologic Revertants of Murine and Avian Sarcoma Virus–Transformed Cells," *J. Virology* 11:218–222.

Varmus et al. 1981, "Retroviruses as Mutagens: Insertion and Excision of a Nontransforming Provirus Alter Expression of a Resident Transforming Provirus," *Cell* 25:23–36.

Varmus et al., 1981, "Revertants of an ASV–Transformed Rat Cell Line Have Lost the Complete Provirus or Sustained Mutations in src," *Virology* 108: 28–46.

Vitaterna et al., 1994, "Mutagenesis and Mapping of a Mouse Gene, Clock, Essential for Circadian Behavior," *Science* 264:719–725.

Wilson et al., 1986, "A Frameshift at a Mutational Hotspot in the Polyoma Virus Early Region Generates Two New Proteins That Define T–Antigen Functional Domains," *Cell* 44: 477–487.

VECTORS FOR GENE TRAPPING AND GENE ACTIVATION

The present application claims priority to the U.S. Provisional Application Ser. No. 60/079,729 entitled "Vectors For Gene Trapping and Gene Activation", filed Mar. 27, 1998.

1.0. FIELD OF THE INVENTION

The present invention relates to the use of a novel 3' gene trap cassette that is incorporated into a recombinant vector. Vectors incorporating the gene trap cassette are important tools for both gene discovery, gene cloning, gene mutation, gene regulation, shuttling nucleic acid sequences throughout the genome, and gene activation and overexpression.

2.0. BACKGROUND OF THE INVENTION

Gene trapping provides a powerful approach for simultaneously mutating and identifying genes. Although vector insertion into the cellular genome can be a random process, gene trap vectors have been designed that select for events in which the gene trap vector has inserted into and mutated a gene. By exploiting the cellular splicing machinery, these vectors remove the large background of insertion events where vectors have not integrated into genes. Most mammalian genes are divided into exons and introns. Exons are the portions of the gene that are spliced into mRNA and encode the protein product of a gene. In genomic DNA, these coding exons are divided by noncoding intron sequences. Although RNA polymerase transcribes both intron and exon sequences, the intron sequences must be removed from the transcript so that the resulting MRNA can be translated into protein. Accordingly, all mammalian, and most eukaryotic, cells have the machinery to splice exons into mRNA. Gene trap vectors have been designed to integrate into introns or genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector encoding the gene has integrated into an intron. The resulting gene trap events are subsequently identified by selecting for cells that can survive selective culture.

Gene trapping has proven to be a very efficient method of mutating large numbers of genes. The insertion of the gene trap vector creates a mutation in the trapped gene, and also provides a molecular tag for ease of identifying the gene that has been trapped. When ROSAβgeo was used to trap genes it was demonstrated that at least 50% of the resulting mutations resulted in a phenotype when examined in mice. This indicates that the gene trap insertion vectors are useful mutagens. Although a powerful tool for mutating genes, the potential of the method was limited by the difficulty in identifying the trapped genes. Methods that have been used to identify trap events rely on the fusion transcripts resulting from the splicing of exon sequences from the trapped gene to sequences encoded by the gene trap vector. Common gene identification protocols used to obtain sequences from these fusion transcripts include 5' RACE, cDNA cloning, and cloning of genomic DNA surrounding the site of vector integration. However, these methods have proven labor intensive, not readily amenable to automation, and generally impractical for high-throughput.

More recently, vectors have been developed that rely on a new strategy of gene trapping that uses a vector that contains a selectable marker gene preceded by a promoter and followed by a splice donor sequence instead of a polyadenylation sequence. These vectors do not provide selection unless they integrate into a gene and subsequently trap downstream exons which provide a polyadenylation sequence. Integration of such vectors into the chromosome results in the splicing of the selectable marker gene to 3' exons of the trapped gene. These vectors provide a number of advantages. They can be used to trap genes regardless of whether the genes are normally expressed in the cell type in which the vector has integrated. In addition, cells harboring such vectors can be screened using automated (e.g., 96-well plate format) gene identification assays such as 3' RACE (see generally, Frohman, 1994, PCR Methods and Applications, 4:S40–S58). Using these vectors it is possible to produce large numbers of mutations and rapidly identify the mutated, or trapped, gene. However, prior to the present invention, the broad exploitation of such vectors has been hampered by the limited number of target genes that can be efficiently trapped.

3.0. SUMMARY OF THE INVENTION

The relative inefficiency of previous 3' gene trap vectors limited the total number of genes that could be rapidly analyzed and identified using such vectors. This inefficiency prompted the development of more efficient methods of 3' gene trapping—methods that allow a greater percentage of genes in the target cell genome to be trapped and rapidly identified by, for example, DNA sequence analysis.

The present invention relates to the construction of a novel vector comprising a 3' gene trap cassette that allows for high efficiency 3' gene trapping. The presently described 3' gene trap cassette comprises in operable combination, a promoter region, an exon (optionally characterized by a translation initiation codon and open reading frame and/or internal ribosome entry site), a splice donor sequence, and, optionally, intronic sequences. The splice donor (SD) sequence is operatively positioned such that the exon of the 3' gene trap cassette is spliced to the splice acceptor (SA) site of a downstream exon or a cellularly encoded exon. Typically, the presently described 3' gene trap cassette will trap cellular 3' exons with sufficient efficiency to enable the facile detection, screening, and identification of at least about 10,000 distinct 3' gene trapped cellular exons (generally representing approximately 10,000 different genes—the number may be reduced by the fact that independent integration events can occur within different introns/exons within the same gene), preferably at least about 15,000 distinct 3' gene trapped cellular exons, more preferably at least about 25,000 distinct 3' gene trapped cellular exons, and most preferably at least about 50,000 distinct 3' gene trapped cellular exons.

Preferably, the exon component of the 3' gene trap cassette will comprise exon sequence and a splice donor sequence derived from genetic material that naturally occurs in an eukaryotic cell.

Additional embodiments of the present invention include recombinant vectors, particularly viral vectors, that have been genetically engineered to incorporate the described 3' gene trap cassette. Preferably, although not necessarily, these vectors will additionally incorporate a selectable marker that allows for maintenance and detection of vector sequence in the target cell.

An additional embodiment of the present invention is the use of the novel 3' gene trap cassette, or vectors comprising the same, to mutate and trap genes in a target cell, population of different target cells, or tissues in vitro or in vivo. As such, general methods of gene mutation, identification, and phenotypic screening are described that use the described 3' gene trap cassette, and vectors comprising the same.

Another embodiment of the present invention is the use of the presently described vectors to activate gene expression in target cells. Additionally, assays are described that employ the described 3' gene trap cassette, or vectors incorporating the same, to activate, genetically or phenotypically select for, and identify new genes.

Additional embodiments of the presently described invention include libraries of eukaryotic cells that have been mutated using the described 3' gene trap cassette or vectors incorporating the same.

4.0. DESCRIPTION OF THE FIGURES

FIG. 1 presents a diagrammatic representation of how the presently described 3' gene trap cassette is spliced to cellular exons after the cassette is incorporated into the target cell genome.

Figure 2:
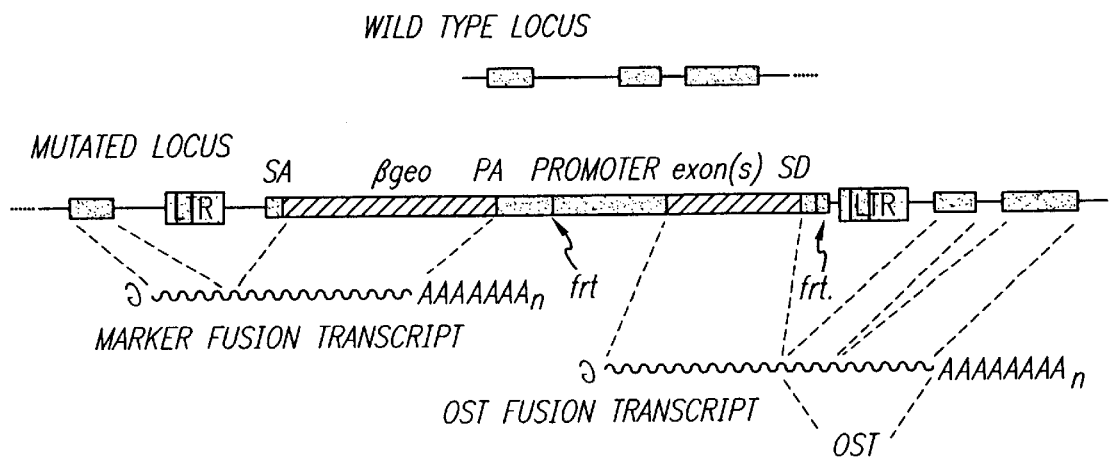

FIG. 2 shows a dual (5' and 3') gene trap vector that incorporates a selectable marker in the 5' trap and the presently described 3' gene trap. FIG. 2 also shows the positions of recombinase recognition, e.g. frt, sites located 5' to the promoter of the 3' gene trap cassette and 3' to the SD of the 3' gene trap cassette.

5.0. DETAILED DESCRIPTION OF THE INVENTION

In the modern age of genomics, gene trapping has proven to be a powerful approach for both grouping gene sequences into functional categories and identifying novel genes. For example, previous results have shown that over half of the gene trap events from embryonic stem cells thus far characterized identify genes that have not been previously discovered. Gene trapping has been used in a variety of cell types to genetically screen for genes that are induced by inductive signals, differentiation events, or phenotypes of interest (i.e., in gene discovery). Additionally, such screens have been used to identify tumor suppressor genes, genes induced by cellular differentiation processes such as hematopoietic and muscle cell differentiation, genes induced by signals that induce cellular events such as B cell activation or apoptosis, and genes activated by small molecules or other compounds. These studies indicate that gene trapping can be used to group genes based upon their function in important cellular and physiological processes. However, the broader exploitation of these screens has been limited by the difficulty of identifying the trapped genes.

Vectors incorporating the presently described 3' gene trap cassette can be used in virtually any type of eukaryotic cell that can be manipulated to insert a gene trap vector into the genome of the cell. For example, vectors that incorporate the presently described 3' gene trap cassette can be used to trap genes in primary animal tissues as well as any other eukaryotic cell or organism including, but not limited to, yeast, molds, fungi, and plants. Additional examples of suitable target cells include, but are not limited to, mammalian, including human, endothelial cells, epithelial cells, islets, neurons or neural tissue, mesothelial cells, osteocytes, lymphocytes, chondrocytes, hematopoietic cells, immune cells, cells of the major glands or organs (e.g., lung, heart, stomach, pancreas, kidney, skin, etc.), exocrine and/or endocrine cells, embryonic and other stem cells, fibroblasts, and culture adapted and/or transformed versions of the above can be used in conjunction with the described vectors. Additionally, tumorigenic or other cell lines can be targeted by the presently described vectors.

Typically, the presently described vectors can be introduced to target cells by any of a wide variety of methods known in the art. Examples of such methods include, but are not limited to, electroporation, viral infection, retrotransposition, microinjection, lipofection, or transfection.

The vectors described in the present invention can also be used in virtually any type of phenotypic or genetic screening protocols both in vitro and in vivo, and the presently described vectors provide the additional advantage of enabling rapid methods of identifying the DNA sequences of the trapped genes.

The sequencing of cDNA libraries has provided many hundreds of thousands of expressed sequence tags (ESTs). These sequence tags typically identify genes or the coding portion of DNA. Since genes are thought to code for most, if not all, potential drug targets, there has been a rush to obtain ESTs identifying all mammalian genes. However, in spite of the wealth of sequence data generated thus far, many genes have proven quite difficult to identify using these random methods because the genes are not expressed, expressed at very low levels, expressed only in specific cell types, or only transiently expressed. Given that gene trapping can detect genes that are not normally expressed in the target cell, gene trapping is an important approach for gene discovery (as demonstrated by the large number of novel sequences that have been identified by gene trapping).

The present vectors are preferably engineered to encode and, optionally, express a marker gene that facilitates the tracking and identification of target cells that incorporate the presently described 3' gene trap cassette. Such markers include, but are not limited to, antibiotic resistance genes, calorimetric marker genes, enzymes (e.g., β-lactamase), or other marker genes that, for example, mediate the direct or indirect expression of fluorescent marker genes such as the gene encoding green fluorescent protein, and assays for detecting the same, which are described, inter alia, in U.S. Pat. No. 5,625,048, herein incorporated by reference. For the purposes of the present disclosure, the term "directly," when used in a biological or biochemical context, refers to direct causation of a process that does not require intermediate steps, usually caused by one molecule contacting or binding to another molecule (which can be a molecule of the same type or a different type of molecule). For example, molecule A contacts molecule B, which causes molecule B to exert effect X that is part of a biological process. For the purposes of the present invention, the term "indirectly," when used in a biological or biochemical context, refers to indirect causation that requires intermediate steps, usually caused by two or more direct steps. For example, molecule A contacts molecule B to exert effect X which in turn causes effect Y.

The marker gene can be incorporated into the described vectors as a self-contained expression cassette including a marker, promoter for expressing the marker, ribosome binding/translation start site, and polyadenylation sequence. Additionally, the marker can be placed in the vector such that it is expressed from a vector promoter, and can optionally be engineered to functionally incorporate an independent ribosome entry site (IRES) that facilitates marker expression.

The presently described vectors can also incorporate a 5' gene trap cassette in lieu of, or in addition to, the marker cassette. The 5' gene trap cassette contains a splice acceptor site located 5' to an exon encoding a selectable marker gene. Preferably, the 5' gene trap cassette will not contain a promoter that expresses the marker, and in such instances the marker can only be expressed if the vector integrates into an intron 5' to the translation start site of the endogenous gene, or if the vector integrates into a downstream intron that is in the correct reading frame such that a fusion protein is created that maintains selectable marker protein function. Such vectors selectively increase the probability that the identified sequence tags begin with sequences 5' to the start of translation. Typically, vectors incorporating 5' gene traps do not contain operative promoters that efficiently express the exon encoded in the 5' gene trap, and/or do not encode a splice donor operatively positioned 5' to the splice acceptor of the exon of the 5' gene trap. Optionally, the selectable marker can be engineered to contain an internal ribosome entry site so that it will be expressed in a manner largely independent of the position in which the vector has integrated into the target cell genome.

One potential limitation of 5' gene trap vectors (vectors designed to trap 5' exons) is that only expressed genes are usually trapped. Accordingly, particularly for the purposes of gene discovery, ES cells are particularly preferred target cells because ES cells are thought to be generally promiscuous in the expression of most genes. If this were true, then most genes could be trapped in ES cells using the vector described in the present invention. To test the percentage of genes that can be detected as expressed in ES cells, 23 ESTs from the GenBank dbest database were selected at random, and primers were synthesized that would identify the genes by PCR. When these primers were used in RT-PCR assays using ES cell RNA, all 23 sets of primers produced product. This indicates that transcripts for all 23 genes could be detected in ES cells. Given that the 23 ESTs screened were selected at random, it is likely that they are representative of genes in general and indicate that a majority of genes that are expressed in other cell types at sufficiently high levels to have been identified by sequencing of conventional cDNA libraries are also expressed in ES cells and are thus presumably identifiable using SAselectable marker poly A (5' gene trap) vectors. However, in those instances where genes are either not expressed or only poorly expressed, a 3' gene trap cassette must be utilized to trap and identify the genes. Moreover, 3' gene trap cassettes enable the rapid procurement of DNA sequence data from the trapped gene by automated means.

Vectors designed to trap 3' exons have made it possible to produce large numbers of mutations and rapidly identify the genes that have been mutated. However, a limitation of previously described forms of such vectors is that only a relatively small number of the genes in the genome can be trapped in a manner that allows subsequent selection for the trapping event, or sequence identification of the trapped gene using 3' RACE. The inherent inefficiency of selecting for trapped 31 exons limits the total number of genes that can be analyzed using these methods, and, as a consequence, only a minor portion of the cellular genome had been effectively trapped/mutagenized using antibiotic selection-mediated 3' exon trapping.

The presently described vectors incorporate a novel 3' gene trap cassette that typically allows an order of magnitude more target genes to be trapped and identified by DNA sequence as compared to previous vectors. The presently described 3' gene trap cassette comprises, in operative combination, a promoter region that mediates the expression of an exon, and an operative splice donor (SD) sequence that defines the 3' end of the exon, and which is spliced to a splice acceptor (SA) sequence of a trapped cellular exon located 3' to the integrated 3' gene trap cassette. Optionally, the exon may additionally encode an open reading frame or gene and/or the exon can incorporate a ribosome binding site or internal ribosome entry sequence to facilitate the expression of the open reading frame. In general, such a ribosome binding site is present 5' to the initiation codon of an open reading frame or gene.

Given that splice donor efficiency can be influenced by intron sequences downstream from the splice donor site, the presently described 3' gene trap cassette can optionally be engineered to contain between about 1 and about several thousand bases of intron sequence adjacent and 3' to the splice donor sequence.

For the purposes of the present invention the term "gene" shall refer to any and all discrete coding regions of the cell's genome, as well as associated noncoding and regulatory regions. Additionally, the term operatively positioned shall refer to the fact that the control elements or genes are present in the proper orientation and spacing to provide the desired or indicated functions of the control elements or genes. Also for the purposes of the present invention, a gene is "expressed" when a control element in the cell mediates the production of functional or detectable levels of mRNA encoded by the gene, or a selectable marker inserted therein. A gene is not expressed where the relevant control element in the cell is absent, has been inactivated, or does not mediate the production of functional or detectable levels of mRNA encoded by the gene, or a selectable marker inserted therein.

Any number of transcriptional promoters and enhancers may be incorporated into the 3' gene trap cassette including, but not limited to, the herpes simplex thymidine kinase promoter, cytomegalovirus (CMV) promoter/enhancer, SV40 promoters, pga promoter, regulatable promoters (e.g., metallothionein promoter), adenovirus late promoter, vaccinia virus 7.5K promoter, and the like, as well as any permutations and variations thereof, which can be produced using well established molecular biology techniques (see generally, Sambrook et al. (1989) *Molecular Cloning Vols. I–III*, Cold Spring Harbor Laboratory Press, Cold Spring Harbor, N.Y., and *Current Protocols in Molecular Biology* (1989) John Wiley & Sons, all Vols. and periodic updates thereof, herein incorporated by reference). Promoter/enhancer regions can also be selected to provide tissue-specific expression.

Generally, the exon of the presently described 3' gene trap cassette is derived from, or corresponds to, nucleotide sequence that is native to, or naturally occurs in, an eukaryotic cell, or, possibly, an animal or plant virus. Preferably, the exon of the presently described 3' gene trap cassette is derived from, or corresponds to, nucleotide sequence that is native to the target cell genome. optionally, the exon is isogenic to sequence in the target cell genome. Where the target cell genome encodes a gene identical or corresponding to the exon of the 3' gene trap cassette, the naturally occurring gene will preferably not be expressed by the target cell at levels that substantially interfere with the amplification and sequencing of the trapped exon sequences in the target cells. For the purposes of the present disclosure, the term "substantially interfere with the amplification and sequencing" shall refer to the fact that the endogenous expression of the naturally occurring exon may hinder but shall not prevent the amplification and sequencing of the trapped exon sequence by 3' RACE protocols, or, optionally, by conventional cloning and sequencing. Additional methods of circumventing this potential complication include the incorporation of an unique sequence within the otherwise naturally occurring exon of the 3' gene trap cassette that can be used as PCR priming site, or to employ a 3' gene trap cassette having an exon that does not naturally occur in the target cell genome.

Alternatively, the exon of the 3' gene trap cassette is derived from nucleotide sequence that is similar or homologous to nucleotide sequence that is native to, or naturally occurs in, the target cell, or the genome of cells from a related species, genus, order, class, phylum, or kingdom. For the purposes of the present invention, an homologous sequence is defined as a nucleic acid sequence that is capable of binding to a target sequence under highly stringent conditions such as, for example, hybridization to filter-bound DNA in 0.5 M $NaHPO_4$, 7% sodium dodecyl sulfate (SDS), 1 mM EDTA at 65° C., and washing in 0.1× SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), or possibly under less stringent conditions, such as, for example, moderately stringent conditions, e.g., washing in 0.2× SSC/0.1% SDS at 42° C. (Ausubel et al., 1989, supra).

The exon of the presently described 3' gene trap cassette may or may not contain a translation start site and/or an open reading frame. Any open reading frames that may be present in the exon can be engineered to incorporate codons that have been optimized to reflect the preferred codon usage of the host cell.

Given that the exon of the presently described 3' gene trap cassette is preferably comprised of sequence native to an eukaryotic, or preferably mammalian, cell, the exon will typically not constitute a marker encoding a protein activity that encodes an antibiotic resistance marker (such as neo, amp, e.g., β-lactamase, tet, kan, and the like) or otherwise confers selectable drug resistance or sensitivity to the host cell (although such a marker can optionally be appended to, for example, the 5' region of the exon).

Alternatively, the exon will generally not encode an enzymatic activity, or reporter gene, that mediates selectable detection via a conventional chromogenic or fluorescent assays (e.g., β-galactosidase, alkaline phosphatase, or horse radish peroxidase) that is not native to the, preferably mammalian, target cell.

The described 3' gene trap cassettes are characterized by a marked improvement in the efficiency of 3' exon trapping. As such, another embodiment of the present invention is a 3' gene trap cassette, and vectors incorporating the same, that are characterized by having the capability of trapping 3' exons with at least about 15 percent of the efficiency with which a similarly situated SAβgeo gene trap cassette traps 5' exons, preferably, at least about 25 percent, more preferably at least about 40 percent, specifically at least about 60 percent, and more specifically at least about 85 percent. For the purposes of the present invention, a similarly situated gene trap cassette is a cassette that is present in a similar relative orientation within a similar vector. Alternatively, similarly situated gene trap cassettes may both be present in same vector.

Any of a variety of quantitative measurements are available to those skilled in the art that can be used to calculate the relative efficiency of the respective 3' and 5' gene trap cassettes as well as the absolute number of genes that can be trapped. For example, one can determine the percentage of target genes identified by the presently described 3l gene trap cassette relative to the percentage of target genes identified by 5' gene traps such as SAβgeo or SAneo and selected using, for example, the antibiotic G418. Alternatively, the percentage of identifiable 3' gene trap events can be compared to the percentage of target cells rendered antibiotic resistant or chromogenically identifiable by SAβgeo-mediated 5' gene trap events.

The functional efficiency of the presently described 3' gene trap cassette can also be quantified by the absolute number of independent gene trap events characterized using the vector. Generally, the presently described vectors allow for the expedient trapping of at least about one to about several hundred genes, typically at least about 1,000 different genes, more typically at least about 3,000, preferably at least about 10,000 genes, more preferably at least about 25,000 genes, specifically at least about 50,000 genes, and more specifically at least about 70,000 genes up to the maximum number of genes present in a given cell or cell type. For example, murine cells are thought to encode about 100,000 genes or more.

Given the extensive number of genes that can be rapidly characterized using the present vectors, additional embodiments of the present invention include gene trapped libraries of cultured animal cells that stably incorporate the presently described 3' gene trap cassette. The presently described libraries may be made by a process comprising the steps of treating (i.e., infecting, transfecting, retrotransposing, or virtually any other method of introducing polynucleotides into a cell) a population of cells to stably integrate a vector containing the 31 gene trap cassette, identifying or otherwise selecting for stably transduced cells, and identifying the trapped 31 cellular exons. In a preferred embodiment, the animal cell libraries comprise mammalian cells, and in a particularly preferred embodiment, the mammalian cells are embryonic stem (ES) cells. Preferably, such libraries are constructed such that each mutated cell in the library harbors a single identifiable 3' gene trap vector/event (although mutated cells harboring multiple gene trap vectors are also contemplated by the present invention).

In an additional embodiment of the present invention, the individual mutant cells in the library are separated and clonally expanded. The isolated and clonally expanded mutant cells are then analyzed to ascertain the DNA sequence, or partial DNA sequence, of the insertionally mutated host gene.

Thus, the invention further provides for the sequencing of at least a portion of every gene mutated in the library. The resulting sequence database subsequently serves as an index for the library. In essence, every group of clonally expanded cells in the library is individually catalogued using the partial sequence information. The resulting sequence is specific for the mutated gene since the present methods are designed to obtain sequence information from exons that have been spliced to the 3' gene trap cassette. The resulting sequence database can be used to identify the mutated gene of interest, or, alternatively, represents a powerful tool for the identification of novel genes. Once identified, the corresponding mutant cell may be taken from the library and studied further as described below.

Generally, indexed libraries of isolated cells, or individual cell types (e.g., ES cells), that have been mutated using the claimed 3' gene trap cassette comprise a collection of at least about 50 different isolated mutant cell culture lines, typically at least about 100, more typically, at least about 500, preferably at least about 1,000, more preferably at least about 5,000, specifically at least about 10,000, more specifically at least about 25,000, and even more specifically at least about 40,000 up to about one to five hundred thousand different isolated and characterized mutant cell culture lines or more.

Preferably, the genomes of the different mutant cell cultures present in a given library are essentially identical (e.g., derived from a common source or inbred strain) except for the location of the inserted gene trap cassette, or vector incorporating the same.

Ideally, the scope of mutagenesis is the entire set of genes in the target cell. Consequently, the resulting sequence database will ideally contain an essentially complete representation of every gene in the target cell. For the purposes of the present invention, the term "essentially complete representation" shall refer to the statistical situation where there is generally at least about an 85–95 percent probability that the genomes of the cells' used to construct the library collectively contain an stably inserted 3' gene trap cassette in at least about 70 percent of the genes present in the target cell genome, preferably at least about 85 percent, and more specifically at least about a 95 percent as determined by a standard Poisson distribution and assuming that the 3' gene trap cassette integrates randomly.

The broad coverage afforded by the present vectors also allows for the broad mutagenesis of the cellular genome of the target cell. Typically, such a broad library of mutated target cells will comprise a collection of mutated cells, or isolated cultures thereof, that collectively represent at least one 3' gene trap mutation (mediated by the described 3' gene trap cassette or vector comprising the same) in each chromosome present in the target cell genome, preferably at least about 3 independent gene trap mutations per chromosome will be collectively present in the library, more preferably at least about 20 independent gene trap mutations are represented, and most preferably at least about 500 independent gene trap mutations per chromosome (up to essentially complete representation) are collectively represented in the library.

The presently described invention allows for large-scale genetic analysis of the genomes of any organism for which there exists cultured cell lines. The described libraries may be constructed from any type of cell that can be transfected by standard techniques or transfected with a recombinant vector harboring the described 3' gene trap cassette. Accordingly, the presently described methods of making, organizing, and indexing libraries of mutated animal cells are also broadly applicable to virtually any eukaryotic cells that may be genetically manipulated and grown in culture.

Where mouse ES cells are used to construct the library, and preferably early passage ES cells, the library becomes a genetic tool for the comprehensive study of the mouse genome. Since ES cells can be injected back into a blastocyst and incorporated into normal development and ultimately the germ line, the mutated ES cells of the library effectively represent collection of mutant transgenic mouse strains (see generally, U.S. Pat. No. 5,464,764 issued Nov. 7, 1995, herein incorporated by reference).

A similar methodology can be used to construct virtually any non-human transgenic animal (or animal capable of being rendered transgenic). Such nonhuman transgenic animals may include, for example, transgenic pigs, transgenic rats, transgenic rabbits, transgenic cattle, transgenic goats, and other transgenic animal species, particularly mammalian species, known in the art. Additionally, bovine, ovine, and porcine species, other members of the rodent family, e.g. rat, as well as rabbit and guinea pig and non-human primates, such as chimpanzee, may be used to practice the present invention.

Transgenic animals and cells produced using the presently described library and/or vectors are useful for the study of basic biological processes and diseases including, but not limited to, aging, cancer, autoimmune disease, immune disorders, alopecia, glandular disorders, inflammatory disorders, ataxia telangiectasia, diabetes, arthritis, high blood pressure, atherosclerosis, cardiovascular disease, pulmonary disease, degenerative diseases of the neural or skeletal systems, Alzheimer's disease, Parkinson's disease, asthma, developmental disorders or abnormalities, infertility, epithelial ulcerations, and viral and microbial pathogenesis and infectious disease (a relatively comprehensive review of such pathogens is provided, inter alia, in Mandell et al., 1990, "Principles and Practice of Infectious Disease" 3rd. ed., Churchill Livingstone Inc., New York, N.Y. 10036, herein incorporated by reference). As such, the described animals and cells are particularly useful for the practice of functional genomics (similar libraries, and methods of making and screening the same, are discussed in U.S. application Ser. No. 08/942,806, filed Oct. 2, 1997 the disclosure of which is herein incorporated by reference in its entirety).

In addition to the study of diseases, the presently described methods, libraries, cells, and animals are equally well suited for identifying the molecular basis for genetically determined advantages such as prolonged life-span, low cholesterol, low blood pressure, resistance to cancer, low incidence of diabetes, lack of obesity, or the attenuation of, or the prevention of, all inflammatory disorders, including, but not limited to coronary artery disease, multiple sclerosis, rheumatoid arthritis, systemic lupus erythematosus, and inflammatory bowl disease.

The presently described 3' gene trap cassette is preferably introduced to target cells as a structural component of any of a wide range of expression vectors that can be randomly or specifically inserted (using, for example, the disclosed recombinase systems) into the target cell genome. Suitable vectors that can be used in conjunction with the presently disclosed 3' gene trap cassette include, but are not limited to, herpes simplex virus vectors, adenovirus vectors, adeno-associated virus vectors, retroviral vectors, lentiviral vectors, pseudorabies virus, alpha-herpes virus vectors, and the like. A thorough review of viral vectors, particularly viral vectors suitable for modifying nonreplicating cells, and how to use such vectors in conjunction with the expression of polynucleotides of interest can be found in the book *Viral Vectors: Gene Therapy and Neuroscience Applications* Ed. Caplitt and Loewy, Academic Press, San Diego (1995). As used herein, the term "expression" refers to the transcription of the DNA of interest, and the splicing, processing, stability, and, optionally, translation of the corresponding mRNA transcript.

Where retroviral vectors are used to deliver the presently described 3' gene trap cassette, the retroviral vectors can be used in conjunction with retroviral packaging cell lines such as those described in U.S. Pat. No. 5,449,614 ("'614 patent") issued Sep. 12, 1995, herein incorporated by reference. Where non-mouse animal cells are to be used as targets for generating the described libraries, packaging cells producing retrovirus with amphotropic envelopes will generally be employed to allow infection of a broad range of host cells. Alternatively, such retroviral vectors can be packaged in conjunction with chimeric integrase molecules as described in U.S. application Ser. No. 08/907,598, herein incorporated by reference. Typically, the LTRs used in the construction of the packaging cell lines are self-inactivating. That is, the enhancer element is removed from the 3' U3 sequences such that the proviruses resulting from infection would not have an enhancer in either LTR. An enhancer in the provirus may otherwise affect transcription of the mutated gene or nearby genes.

An additional advantage of using viral, and particularly retroviral, infection (e.g., biological methods) to deliver recombinant viral vectors incorporating the 3' gene trap cassette is that viral infection is more efficient than standard nonbiological methods of delivering genetic material to target cells. Where recombinant genetic material is delivered by retroviral infection, the recombinant RNA genome of the retrovirus is reverse transcribed within the target cell, and the retroviral integrase packaged within the infecting virus subsequently mediates the essentially random integration of the vector (and 3' gene trap cassette) into the target cell genome. Accordingly, additional embodiments of the present invention include methods of inserting recombinant vectors incorporating the described 3' gene trap cassette that are mediated by integrase or recombinase activities that are either exogenously added to the target cell, or do not naturally occur within the target cell.

Representative retroviral vectors that can be adapted to incorporate the presently described 3' gene trap cassette are described, inter alia, in U.S. Pat. No. 5,521,076, and U.S. applications Ser. Nos. 08/942,806, filed Oct. 2, 1997, and 08/907,598 filed Aug. 8, 1997 (all of which further disclose screening protocols that can be used to assay for specific gene trap events either biochemically or phenotypically) the disclosures of which are herein incorporated by reference. Typically, the direction of transcription of gene trap cassettes incorporated into retroviral vectors is opposite to that of the direction of normal retroviral transcription; however, retroviral vectors are contemplated where one or more gene trap cassettes are incorporated in the same orientation as normal retrovirus transcription. Typically, the reason for placing a gene trap cassette in an opposite orientation relative to the LTRs is that the presence of engineered controlled elements such as polyadenylation signals, splice sites and the promoters, can interfere with the proper transcription of the retroviral genome in the packaging cell line, and subsequently reduce retroviral titers. Additionally, since a 'cryptic' splice donor sequence is found in the inverted LTRs, this splice donor can optionally be removed by site specific mutagenesis so that it does not adversely effect trapping related splicing events. Optionally, the LTR promoter and/or enhancer function can be inactivated by deleting all or a portion of the promoter and/or enhancer sequences.

The presently described 3' gene trap cassette, and vectors incorporating the same, provide an important tool for conducting genetic screens in any cell or cell line that contains splicing machinery and genes split by introns. The presently described gene trap vectors represent a particularly important technological breakthrough because the incorporation of the described 3' gene trap cassette allows for the rapid identification of roughly 13 fold more genes than can be facilely obtained using conventional 3' gene trap vectors that utilize antibiotic selection. Combined with the frequency of obtaining novel gene sequences, the observed increase in identifiable gene trap targets will provide sequence information for large numbers of novel genes and gene sequences. Additionally, each of these novel sequences represent both a "knock out" cell and, in the case of embryonic stem cells, a potential "knock out" embryo or animal, as well as a potential drug target.

The presently described 3' gene trap cassette contains a promoter directing the expression of one or more exons (optionally encoding one or more open reading frames) that are followed by a splice donor sequence (FIG. 1). Preferably, the exon or exons have been designed to mimic an exon of a gene. Generally, the exon or exons (and part of the intron following the exon(s)) and splice donor sequence are derived from a naturally occurring gene; however synthetic exons designed to mimic real exon(s) may also be utilized. For example, such exons might be designed and constructed de novo or by modifying existing exons to incorporate a high efficiency, or consensus, ribosome binding site, to add an IRES sequence, to create an open reading frame, to optimize codon usage, to engineer one or more restriction sites that do not alter the amino acid sequence encoded by the open reading frame, or to engineer an alternative or consensus splice donor sequence into the exon.

A particularly novel aspect of the presently described vector is the use of a 31 gene trap cassette that employs an exon that does not code for a marker that provides a selectable growth advantage to the target cell (e.g., an antibiotic resistance gene). All previously reported gene trapping vectors have used selectable marker sequences. As presently shown, 3' gene trap cassettes incorporating open reading frames of noneukaryotic origin typically display a markedly reduced efficiency of 3' exon trapping.

Consequently, vectors employing the presently described 3' gene trap cassette greatly increase the number of target genes that can be trapped and rapidly identified by sequence tagging.

Vectors contemplated by the present invention are preferably engineered to contain sequence components, or markers, that provide for the selection of cells that have incorporated the marker into the chromatin of the cell. In general, such selectable markers enable facile and overt methods of identifying and selecting for eukaryotic cells that incorporate and express the proteins encoded by the selectable markers relative to like cells that do not express the selectable markers. Examples of such overt methods of selection include antibiotic, colorimetric, enzymatic, and fluorescent selection of cells that have integrated a gene trap event. One example of such a selectable marker gene is βgeo, but any of a number of other selectable markers can be employed (for example, see U.S. Pat. No. 5,464,764 herein incorporated by reference).

The specifically described vectors employ SAβgeo which is comprised of a selectable marker gene preceded by a splice acceptor sequence and followed by a polyadenylation sequence (FIG. 2). Alternatively, SAIRESβgeo can be used which further incorporates an internal ribosome entry site upstream from the βgeo gene. Both of these 5' gene traps efficiently mutate genes and can be used to follow expression of the trapped gene.

The presently described vectors preferably incorporate a 3' gene trap cassette that provides a method of gene identification that increases the probability of identifying the 5' ends of the translational open reading frames of genes. This is significant because the 5' ends of genes often code for the signal sequence that is found in secreted and transmembrane proteins. This group of genes is highly enriched for potential protein therapeutics and drug targets. Given that 5' noncoding sequences average about 100 bp in length and the average length sequence tag is about 500 bp, tagged sequences generated using the presently described vectors will typically identify the 5' portion of the tagged open reading frame. This is especially valuable since 5' ends of genes can be difficult to obtain due to complicating factors such as high GC content, secondary structure, and reverse transcriptase's lack of processivity.

A large number of traps in known genes were made using vectors that incorporate the presently described 3' gene trap cassette. When the sequences of the trapped 3' exons were analyzed, 93% of the trap sequence tags that matched cDNA sequences in Genbank contained the same or additional 5' sequence. This confirms that the described 3' gene trap cassette can be used to identify and characterize the 5' termini of genes. In fact, the gene trap methods of the present invention identify the 5' end of genes better than or equal to other methods described to date.

One of the major challenges in the field of genomics remains the isolation and cloning of full length cDNAs for all genes. To date, this has required the production of cDNA from a wide variety of tissues, followed by the subsequent sequencing of the individual cDNAs. As described above, using such methods it can be very difficult to obtain the 5' ends of cDNAs. Additionally there is the problem that in order to obtain a complete repertoire of cDNAs, individual cDNA libraries must made from essentially every differentiated cell type and at every developmental time point because genes must be expressed in order to be cloned as ESTs.

The 3' gene trap cassette of the present invention can be used for the creation of cDNA libraries. When introduced to cells in culture, the 3' gene trap cassette produces transcripts of genes independent of whether or not they are normally expressed in that cell type. The expression levels of the various trapped genes are normalized by the inserted promoter so that even genes that are only expressed at very low levels are identified. Using the presently described methods and vectors, one can obtain broad cDNA coverage of the target cell genome from a single library without having to independently produce multiple cDNA libraries from multiple cell types that were grown under multiple conditions. The presently described 3' gene trap cassette can be inserted into the genome of the tissue culture cells and methods can be used which only allow cDNA arising from trapped genes to be subcloned into the cDNA library. These methods will increase coverage of cDNAs while substantially decreasing the labor involved to produce the libraries. As discussed above, the presently described methods are also particularly useful in obtaining the 5' ends of genes, and thus optimize the chances of obtaining full length cDNAs.

When vectors containing both SAβgeo (as a 5' exon trap) and PGKpuroSD (as a 3' exon trap) were tested, it was found that 13 times as many G418 resistant colonies were obtained as compared to puro resistant colonies. This indicated that, in many cases, when SAβgeo trapped a gene, the puro SD portion of the gene trap vector was unable to effectively trap the 3' portions of the same gene (as evidenced by the failure to confer puromycin resistance to the target cell). In addition, when the G418 resistant colonies were isolated and subjected to 3' RACE to determine whether puro was splicing into downstream exons but not at sufficiently high levels to provide puro selection, it was found that only about 10% of the colonies yielded a 3' RACE product. Moreover, the sequence data indicated that splicing was not occurring in the majority of cases. These data indicated that the PGKpuroSD 3' gene trap cassette could only splice into and trap downstream exons of genes with limited efficiency. Similar inefficiencies have also been observed using a variety of other selectable markers in addition to puro. This could be due to the fact that most selectable markers are derived from microorganisms. For example, the puro gene was derived from *Streptomyces alboniger* and therefore incorporates a codon usage that is distinct from that typically used by mammalian cells.

In order to test whether codon usage was responsible for the observed inefficiency in splicing, a puro gene was synthesized that incorporated an optimal mammalian codon usage. However, 3' gene trap cassettes that incorporated the modified puro exon were not efficiently spliced. Another possible reason for inadequate splicing is that the puromycin marker is 700 bp long whereas the average length of a first exon is only about 100 bp. Thus, it further remained possible that placing a selectable marker gene next to a promoter hindered the optimal recognition of the puro exon and splice donor sequence by the splicing machinery.

Given the important discovery that the cellular RNA splicing machinery could only process the puro gene exon with limited efficiency, we reasoned that 3' gene trap cassettes incorporating naturally occurring mammalian exons might exhibit markedly enhanced splicing, and hence trapping, efficiencies. To test this hypothesis, a 3' gene trap cassette was engineered that replaced the puro exon and splice donor site with a naturally occurring mouse exon with a native splice donor sequence as well as a portion of the naturally occurring intronic sequence following the splice donor site (the first exon of the mouse btk gene, nucleotides 40,043 to 40,250 of Genbank accession number bIMU58105). This cassette was subsequently inserted 3' to the SAβgeo gene in a viral gene trap vector. The first exon of the mouse btk gene was selected because it is about the size of an average mammalian first exon and, importantly, it had previously been determined that, although it naturally occurs in the murine genome, the btk gene is not expressed in murine ES cells. This feature is important because if it were expressed in ES cells, the 3' RACE product would always be contaminated with btk sequence from the endogenous gene and might hinder the ability to identify the trapped genes.

Although the first exon of btk has been specifically exemplified herein, the present invention is not limited to this exon. Virtually any naturally occurring exon of an eukaryotic gene, series of exons from one or more eukaryotic genes, or synthetic exon or exons that are readily recognized and efficiently processed by the target cell RNA processing and expression machinery can be incorporated into the presently described 3' gene trap cassette.

Given that typical antibiotic resistance markers are not native to animal or mammalian cells, markers that confer antibiotic resistance or sensitivity (Herpes thymidine kinase) to mammalian target cells are generally not preferred for incorporation into the presently described 3' gene trap cassettes. Similarly, given that typically available enzymatic markers that might be used in chromogenic assays for the detection and selection of gene trap events (such as β-galactosidase, horse radish peroxidase, bacterial alkaline phosphatase, etc.) are also not native to the mammalian genome, such genes are not preferred for the practice of the present invention. However, if suitable genetic manipulations were found that increase the efficiency with which transcripts encoding the above selectable and enzymatic markers are processed and expressed by mammalian cells, such markers could be used to practice the claimed invention. Although the above selectable markers and enzymatic reporters are preferably not part of the presently described 3' gene trap cassette, they can be used as part of the 5' gene trap component in combination with the described 3' gene trap cassette.

Exons that can be incorporated into the presently described 3' gene trap cassette can be taken or derived from sequences that naturally occur in any of a wide variety of eukaryotic cells (e.g., yeast, insect, fungi, plants, birds, reptiles, fish, etc.), although animal cells, specifically mammalian cells, are typically preferred. Alternatively, exons can be designed and synthesized such that they can be efficiently and functionally processed by the mRNA processing machinery of the eukaryotic target cell (e.g., splicing, capping, polyadenylation, transport, and degradation).

Another embodiment of the present invention is that the 3' gene trap cassette can be used to screen for both gain or loss of function in animals, e.g., mice, and cultured cells. Because the promoter of the 3' gene trap cassette directs the expression of an exon that lacks a translation start site, a given gene can be either overexpressed or insertionally inactivated (mutated) depending on where the vector has integrated within the gene. If the vector lands in an intron preceding the start of translation, it can cause overexpression of the full open reading frame encoding the cellular protein. Using these types of trapping events one can conduct genetic screens based upon gene overexpression. These screens could be done in cell culture or in mice, for example, in order to discover genes that play significant roles in disease processes. For example, these screens could be used to identify oncogenes by introducing the 3' gene trap cassette into primary embryo fibroblasts and selecting for an ability to grow in soft agar. Alternatively, assaying for cells able to escape cellular senescence would also allow the identification of potential oncogenes.

In order to demonstrate that the present vectors can be used to select for trapping events that result in gene overexpression, an experiment was conducted to determine whether genes could be trapped that allow expression of factors that promote ES cell differentiation. Large numbers of genes were trapped in cell culture on tissue culture plates. Multiple plates were infected in parallel and the resulting plates were observed for ES cell differentiation. Some plates showed almost no differentiation whereas some plates would have 100w differentiated ES cells. This differentiation is likely the result of overexpression of a gene that is either a differentiation factor or causes the ES cells to produce a differentiation factor and pump it into the media resulting in differentiation of all the cells on the dish. Importantly, this also demonstrates that the 3' gene trap system can be used to activate and screen for secreted molecules that produce specific biological responses by testing supernatants of the gene trap pools. Screening for ES cell differentiation factors is one example but this technique can be used to identify secreted molecules involved in any cellular response of interest. One could for example screen for secreted molecules that induce apoptosis or hematopoietic cell differentiation.

Given the increased expression afforded by the presently described 3' gene trap cassette, an additional application of the presently described 3' gene trap cassettes is gene activation. For example, after suitable animal cells are treated or infected with vectors that incorporate the described 3, gene trap cassette, if the vector randomly integrates into the 5' intron of an otherwise relatively quiescent gene, the gene can be "activated" and overexpressed by the regulatory elements, e.g., enhancer/promoter elements incorporated into the 3, gene trap cassette. Using such random, or biased random (see U.S. applic. Ser. No. 08/907,598) gene activation, modified animal cells, including human cells, can be produced that overexpress any of a wide variety of natural cellular products.

Products that are particularly deemed useful for such application include, but are not limited to, erythropoietin (epo), tPA, cytokines, interleukins, tumor suppressors, chemokines, secreted molecules, G-CSF, GM-CSF, nerve growth factor (NGF), ciliary neurotropic factor (CNTF), brain-derived neurotropic factor (BDNF), interleukins 1–2 and 4–14, tumor necrosis factor-$\alpha$ (TNF-$\alpha$), $\alpha$ or $\gamma$ interferons and the like, leptin, and factors VIII and IX.

The activation of quiescent genes, overexpression, or abnormal expression of genes by the 31 gene trap cassette can also be used to study gene function within an organism. Gene overexpression may be used to study gene function, and by trapping genes with the 3' cassette, genes can be overexpressed within an organism. The overexpression may cause a phenotype in the organism that sheds light on the function of the gene. For example, the specifically described retroviral vector contains the PGK promoter which is ubiquitously expressed. When a gene is trapped in ES cells and the ES cells are subsequently used to make mice, the mice will overexpress the trapped gene ubiquitously. Further modifications could be made for instance to use a promoter that is tissue-specific rather than the PGK promoter in order to overexpress the trapped gene in a tissue-specific manner. The albumin promoter could be used for liver-specific overexpression. Additionally, a signal sequence could be added to the 3' trapping cassette to cause secretion of the trapped gene's protein product from the cell into the extracellular space, into the bloodstream, or mammary excretions. This could facilitate the understanding of gene function.

Since overexpression is one possible outcome of a gene trap event using the 3' gene trap cassette, it is useful to be able to remove the 3' trap/overexpression component. This can be accomplished by flanking any essential component of the 3' trap cassette (essential components may include the promoter, the exon, the splice donor, the intronic sequence or the entire cassette) with recombinase sites such as those recognized by the flp or cre recombinases. In this way, the addition of the corresponding recombinase in cells or in the organism allows one to reverse or remove overexpression as desired.

For gene activation, a generic 3' gene trap cassette can be employed that incorporates an exon that is native to, or compatible with the biology of, the target cell, or a specific 3' gene trap cassette can be constructed that utilizes a specific exon and splice donor site from a known gene. Optionally, given that gene activation using 3' gene traps typically requires that the vector integrate or insert upstream (5') from the translation start site of the activated gene, the gene activation exon will preferably rot incorporate a functional translation start site, or will only incorporate a nominally functional translation start site capable of mediating only incidental levels of translational activity. Alternatively, the incorporation of an internal ribosome entry site into the exon can result in the over expression of the 3' trapped, or activated, gene.

Where a fusion product between the 3' gene trap exon and a downstream cellularly encoded exon (e.g., that only encodes a particular domain of the protein product of the "activated" gene) is desired, the gene trap vector will typically incorporate a functional translation start site or internal ribosome entry site and translation start site.

Alternatively, in those instances where the described vectors integrate downstream from the translation start site, the gene will be mutated, and screens to detect such loss of function can be employed. An example of this approach would be to mutate fibroblasts, for example, with the present vectors and screen for hits that allow growth in soft agar. In this way genes encoding tumor suppressors could be identified. Although only 1 of 2 alleles will typically be trapped, the genome of cells in culture is often unstable and, through selection, events can be found in which the second allele is lost. This makes it possible to also screen for recessive phenotypes.

The gene activation capabilities of the presently described vectors have further application for selective gene discovery. For example, proliferation deficient cells (e.g., tumor suppressor or DNA repair knockout cells, etc.) can be infected with the presently described gene activation vectors. The infected cells can subsequently be screened for cells/colonies that display a partially or fully corrected proliferation phenotype. When cells displaying the corrected phenotype are identified, the "activated" genes responsible for correcting the proliferation deficient phenotype can be rapidly identified by DNA sequencing using, for example, 3' RACE. Typically, genes that partially or fully correct a DNA repair mutation (mutations often associated with cancer in animals and humans), are more likely to encode a tumor suppressor, or possibly oncogene, activity (see generally, Selten et al., 1985, EMBO J., 4(7):1793–1798).

Conversely, cancerous or transformed cells (or cell lines) can be infected with the described gene activation vectors and subsequently subject to various cytotoxic agents that are toxic to growing, or rapidly growing, cells (see generally Wilson et al., 1986, Cell, 44:477–487; Stephenson et al., 1973, J. Virol., 11:218–222; Sacks et al., 1979, Virology, 97:231–240; Inoue et al., 1983, Virology 125:242–245; Norton et al., 1984, J. Virol., 50:439–444; Cho et al., 1976, Science, 194:951–953; Steinberg et al., 1978, Cell 13:19–32; Maruyama et al., 1981, J. Virol., 37:1028–1043; Varmus et al., 1981, Cell, 25:23–26; Varmus et al., 1981, Virology, 108:28–46; Mathey-Prevot et al., 1984, J. Virol., 50:325–334; and Ryan et al., 1985, *Mol. Cell. Biol.*, 5:3477–3582. Preferably, the infected cells are exposed to the cytotoxic or chemotherapeutic agents under conditions where cells that have reverted to a non-transformed phenotype are contact inhibited, and are less susceptible to cytotoxic agents present in the culture medium. This further contributes to the preferential elimination of rapidly growing or transformed cells and, after several cycles, the eventual isolation of cells that have partially or fully reverted to the noncancerous or nontransformed phenotype. The "activated" genes responsible for correcting the transformed phenotype, or suppressing the tumorigenic phenotype, can subsequently be rapidly identified by DNA sequencing using the described 3' RACE protocols.

The presently described methods are also useful for identifying the genetic basis of cancer. Cancers that may be studied, and potentially corrected, using the presently described methods include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposils sarcoma, moles, dysplastic nevi, lipoma, angioma, dermatofibroma, keloids, psoriasis; Breast: carcinoma and sarcoma, and Adrenal glands: neuroblastoma.

Modifications to the above studies include the use of retroviral gene trapping vectors in conjunction with a chimeric integrase that targets, or biases, retroviral integration to genes regulated by specific control sequences or transcription factors. For example, the presently described retroviral gene activation vectors can be packaged into a virus incorporating a p53-chimeric integrase (as described in U.S. applic. Ser. No. 08/907,598) that preferentially targets vector-mediated gene activation to genes regulated by this known tumor suppressor activity.

Appropriately modified, the presently described vectors additionally provide a vehicle for placing any DNA sequence throughout the target cell genome and rapidly identifying where the vectors have integrated. A growing number of DNA sequences have been identified that one might wish to place throughout the genome. Examples of such sequences include recombination sites such as frt sites or lox P sites respectively identified by flp and cre recombinases. Although these sites can be placed throughout the genome by homologous recombination or other transformation methods, the present invention allows for the rapid identification and cataloging of the integration sites using automated processes. These recombination sites can be used for specific DNA insertion or, along with insertions in other positions, and they can be used to create chromosomal rearrangements such as inversions, deletions and translocations. Thus the presently described vectors are particularly useful for studying gene function through chromosomal rearrangements. Other sequences one might wish to place throughout the genome include, but are not limited to, tet, ecdysone, or estrogen receptor DNA binding sites or response elements. These sites are commonly used for inducing or repressing gene expression and by placing these sites throughout the genome, preferably in tens of thousands of different genes, will provide an opportunity to create conditional or tissue-specific regulation of gene expression.

Another aspect of the present invention places a gene encoding a recombinase activity (e.g., flp or cre, etc.) into the vector containing the described 3' gene trap cassette. The recombinase gene can be expressed in a manner similar to that described for the marker genes, supra. In brief, the recombinase can be expressed from an independent expression cassette, can be incorporated into a 5' gene trap, or can be expressed from a vector promoter. Depending on the strategy employed to express the recombinase, it can be present in the vector either 5' or 3' from the 3' gene trap cassette. By incorporating the recombinase gene into the described gene trap vectors, a collection, or library, of mutated cells can be obtained that express the recombinase in essentially the same pattern as the various trapped genes.

These are just a few examples of how the presently described vectors can be used to place any DNA sequence throughout the genome in a manner that allows for the rapid identification of where the vectors have integrated into the target cell chromosome.

Another aspect of the present invention is the ability to produce mutations that can be switched on and off temporally and spatially in cells or in an organism or animal. The ability to mutate a gene only in a specific place or at a specific time has important implications for understanding gene function. For example, the orientation of SAβgeo within an intron regulates its ability to trap, and thus mutate, the normal transcript produced by the trapped gene. Suitably oriented frt recombinase sites can be used in conjunction with flp recombinase to effect the above genome rearrangements (i.e., "flip" the gene trap cassette and thus turn the mutation "on" or "off"). Alternatively, the cre/lox system, for example can also be employed.

To validate the above concept, a vector was constructed that placed the SAβgeo cassette within two inverted lox sites. These sites are recognized by the cre recombinase which can effectively flip DNA sequences located in between the lox sites. A retroviral vector containing SAβgeo flanked by inverted lox sites was integrated into an intron of the HPRT gene by homologous recombination. When SAβgeo was present in the forward orientation, HPRT function was abolished as demonstrated by survival of cells in the presence of 6-thioguanine. However, when cre recombinase was expressed in these cells, the orientation of SAβgeo was flipped to the reverse orientation and HPRT function was regained as demonstrated by growth of cells in HAT containing medium. Thus, the HPRT gene was effectively switched off or on by flipping the orientation of SAβgeo. Accordingly, an additional embodiment of the present invention is drawn to vectors that enable the selective and reversible modulation of gene expression. Using a similar methodology, gene trap mutations can also be made conditional or tissue-specific by linking recombinase expression, and hence the flipping of SAβgeo, for example, to various stimuli/control elements.

An alternative strategy for using the presently described vectors for tissue-specific or regulatable expression is to place specific DNA binding sites such as frt or lox sites within the LTRs. With lox sites in the LTRs, once an insertion is made and identified, the cre recombinase, for example, can be added and used to remove the entire insert except for one LTR containing a single frt or lox site. Additionally, a DNA response element that allows regulatable gene expression can be incorporated, wholly or in part, in conjunction with the recombinase sites. When the vector or gene trap insert is removed by the recombinase activity, the same recombination event that results in the production the single LTR will also produce a functional DNA response element. This single LTR does not interfere with gene function, but the DNA element can be used to modulate gene expression. Typical DNA elements or operators used for modulating eukaryotic gene expression include the tet, ecdysone or estrogen DNA binding sites. The presence of the tet operator in combination with the tet repressor protein would allow the expression of the gene to be modulated up and down. This can be carried out in mice by breeding the line of mice carrying the LTR insertion with lines of mice expressing the tet repressor either ubiquitously or only in specific tissues.

Another embodiment of the present invention is based on the fact that the flp recombinase, for example, can mediate the replacement of frt flanked integrated vector sequences with exogenously added frt flanked sequences. Accordingly, once a suitably constructed vector (incorporating flanking recombinase sites) is incorporated into a given region of the target cell genome, virtually any of a wide variety of DNA sequences (i.e., promoters, enhancers, IRES, response elements, etc.) that also incorporate the same flanking recombinase sites can be exchanged into or out of the vector by employing the proper recombinase protein.

As is evident, vectors, particularly retroviral vectors, incorporating the presently described 3' gene trap cassette can be used to mutagenize, activate, or control the expression of endogenous genes in a wide variety of eukaryotic target cells. Accordingly, the presently described vectors are particularly useful to practice molecular genetic techniques in higher eukaryotes such as birds, fish, and mammals. Examples of the such molecular genetic techniques include both in vitro and in vivo screens for gene activation, mutation, and regulation.

For example, CD4 positive human T cells can be infected with the presently described vectors in vitro, and subsequently infected with a cytopathic strain of human immunodeficiency virus (HIV). Cells that are capable of surviving HIV infection, can be isolated and rapidly screened for genetic mutations that are associated with HIV resistance.

Another screening strategy that can be employed in vitro is mutating transformed cells with the described gene trap vectors and selecting for mutations that prevent rapid proliferation of the transformed cells. This strategy can be used to identify oncogenes or tumor suppressor genes. After mutation of the cells, various chemicals can be used to kill cells that divide rapidly in order to select for insertions in genes that play a role in cell proliferation and the transformed phenotype. One example of a chemical that kills rapidly proliferating cells is bromodeoxyuridine (BrdU), Pestov and Lau, 1994, Proc. Natl. Acad. Sci., USA, 91(26): 12549–12553. BrdU preferentially intercalates into the DNA of rapidly dividing cells and, after the addition of Hoechst 33258, treatment with fluorescent light negatively selects against rapidly dividing cells while simultaneously selecting for slow growing cells.

An in vivo assay contemplated by the present invention includes the application of vectors employing the 31 gene trap cassette to mutagenize and screen animals in vivo. In these assays, the present vectors are used in place of, or in addition to classical chemical mutagens such as, for example, ENU (see generally, Vitaterna et al., 1994, Science, 264:719–725). For example, test animals can be infected in various locations, and with varying concentrations of the presently described viral vectors. Preferable modes of administration include oral, intranasal, rectal, topical, intraperitoneal, intravenous, intramuscular, subcutaneous, subdermal, intracranial, intrathecal, and the like. The aberrant cellular phenotypes resulting from such mutagenic stimuli can then be identified, isolated, and screened. Where tumor cells are observed and isolated, 3' RACE can be used to rapidly identify the mutation associated with the tumorigenic phenotype, and thus identify a candidate tumor suppressor gene or potential oncogene.

An additional in vivo application of the presently described vectors involves the generation of mutant transgenic, and somatic transgenic, cells and animals that are abnormally resistant or susceptible to infection by pathogens causing infectious disease.

Another powerful endpoint of the present invention is the large scale production of mutant nonhuman transgenic animals. Such nonhuman transgenic animals may include, for example, transgenic pigs, transgenic rats, transgenic rabbits, transgenic cattle, transgenic goats, and other transgenic animal species such as birds and fish, particularly mammalian species, known in the art. Additionally, bovine, ovine, and porcine species, other members of the rodent family, e.g. rat, as well as rabbit and guinea pig and non-human primates, such as chimpanzee, may be used to practice the present invention. Particularly preferred animals are rats, rabbits, guinea pigs, and most preferably mice. Both somatic cell transgenic animals (see above), and germ line transgenic animals are specifically contemplated. Additionally, such animals are a source of tissues and cells for further gene trapping studies using cultured cells.

The production of mutations in mouse embryonic stem cells by homologous recombination is well established and has proven useful for studying gene function in a mammalian system. However, homologous gene targeting suffers from a number of limitations. One such limitation is the need for a gene to be both known and mapped in order to determine exon/intron structure of the genomic sequence. Even when a gene and its structure are known, a targeting vector must be made for each individual gene one wishes to mutate. This limits the speed at which large numbers of genes can be mutated by homologous recombination. The presently described methods of non-homologous, or essentially random, 3' gene trapping and mutation do not suffer from the above limitations. Generally, randomly inserted vectors can be distinguished from vectors designed for homologous recombination by the fact that randomly integrated vectors generally lack the extensive regions of homologous targeting sequence typical of DNA vectors designed to insert sequence by homologous recombination (see, for example, U.S. Pat. No. 5,733,761 herein incorporated by reference).

Other methods can be used to create mutations in mice. These include chemical or radiation induced mutations which can be used to mutate genes without any prior knowledge of the gene. These mutations can be made on a large scale but often require lengthy and involved processes to identify the mutated genes by, for example, positional cloning. Additionally, these mutations are identified only after large numbers of mice are screened for phenotypes. This necessitates a large mouse colony, the great expense of maintaining this colony, and time for breeding animals. Methods are required that allow the rapid mutation of genes regardless of prior knowledge of the gene and allow the gene to be easily identified. Gene trapping as described in the present invention confers the ability to mutate large numbers of genes and to identify these mutations while still in embryonic stem cells before incurring the prohibitive costs of large scale mouse production. Mice can be subsequently be produced from ES cells containing gene trap mutations in the most interesting genes, and the resulting phenotypes can be rapidly identified and characterized. The resulting transgenic mice can subsequently be bred with other mouse strains, and, back crossed to produce congenic or recombinant congenic animals that allow for the evaluation of the gene trap mutation in different genetic backgrounds. A representative listing various strains and genetic manipulations that can be used to practice the above aspects of the present invention (including the ES cell libraries) is "Genetic Variants and Strains of the Laboratory Mouse" 3rd Ed., Vols. 1 and 2, 1996, Lyon et al., eds., Oxford University Press, NY, N.Y., herein incorporated by reference in its entirety.

Given that altered cellular phenotypes may be associated with the presently described methods of gene trapping and activation, additional aspects of the invention are the use of screening assays to detect altered cellular and animal phenotypes. Altered phenotypes can also be detected upon exposing the mutated cells and animals to exogenous materials and compounds. Additionally, the gene/proteins associated with the mutant phenotypes can be isolated and subject to further biochemical analysis to identify drug candidates that can alter, replace, interact with, inhibit, or augment the normal function of the protein.

The following assays are designed to identify compounds that interact with (e.g., bind to) extracellular or intracellular proteins. The compounds which can be screened in accordance with the invention include but are not limited to peptides, antibodies and fragments thereof, prostaglandins, lipids and other organic compounds (e.g., terpines, peptidomimetics) that bind to or mimic the activity triggered by the natural ligand (i.e., agonists) or inhibit the activity triggered by the natural ligand (i.e., antagonists); as well as peptides, antibodies or fragments thereof, and other organic compounds that mimic the natural ligand for a given receptor or signal transduction protein.

Such compounds may include, but are not limited to, peptides such as, for example, soluble peptides, including but not limited to members of random peptide libraries (see, e.g., Lam et al., 1991, Nature, 354:82–84; Houghten et al., 1991, Nature, 354:84–86), and combinatorial chemistry-derived molecular library peptides made of D- and/or L-configuration amino acids, phosphopeptides (including, but not limited to members of random or partially degenerate, directed phosphopeptide libraries; see, e.g., Songyang et al., 1993, Cell, 72:767–778); antibodies (including, but not limited to, polyclonal, monoclonal, humanized, anti-idiotypic, chimeric or single chain antibodies, and FAb, $F(ab)_2$ and FAb expression library fragments, and epitope-binding fragments thereof); and small organic or inorganic molecules.

Other compounds which can be screened in accordance with the invention include but are not limited to small organic molecules that are able to gain entry into an appropriate cell and affect the expression of a gene (e.g., by interacting with the regulatory region or transcription factors involved in gene expression); or such compounds that affect the activity of a gene by inhibiting or enhancing the binding of accessory molecules).

Computer modeling and searching technologies permit identification of compounds, or the improvement of already identified compounds, that can modulate the expression or activity of a given gene. Having identified such a compound or composition, the active sites or regions are identified. Such active sites might typically be the binding partner sites, such as, for example, the interaction domains of a protein with its cognate ligand. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination thereof, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. The compounds found from such a search generally identify modulating compounds, or genes encoding the same, that are selected for further study or gene targeting.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of regulatory protein interactions, and related transduction factors will be apparent to those of skill in the art.

Representative examples of molecular modeling systems include the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

Although described above with reference to design and generation of compounds which could alter binding, one could also screen libraries of known compounds, including natural products or synthetic chemicals, and biologically active materials, including proteins, for compounds which are inhibitors or activators of the proteins and genes (and gene trapped cells expressing or failing to express the same) being studied using the presently described tools and methods.

In vitro systems can be designed to identify compounds capable of interacting with (e.g. binding to) the regulatory proteins identified using the subject methods. The identified compounds may be useful, for example, in modulating the activity of wild type and/or mutant gene products. In vitro systems may also be utilized to screen for compounds that disrupt normal regulatory interactions.

The assays used to identify compounds that bind to regulatory proteins involve preparing a reaction mixture of a given protein and the test compound under conditions and for a time sufficient to allow the two components to interact and bind, thus forming a complex which can be removed and/or detected in the reaction mixture. The protein used can vary depending upon the goal of the screening assay. For example, where agonists of the natural ligand are sought, a full length protein, or a fusion protein containing a protein or polypeptide that affords advantages in the assay system (e.g., labeling, isolation of the resulting complex, etc.) can be utilized.

The screening assays can be conducted in a variety of ways. For example, one method to conduct such an assay would involve anchoring the protein, polypeptide, peptide or fusion protein or the test substance onto a solid phase and detecting binding between the protein and test compound or mutant cell. In one embodiment of such a method, the receptor protein reactant may be anchored onto a solid surface, and the test compound, which is not anchored, may be labeled, either directly or indirectly. In another embodiment of the method, the test protein is anchored on the solid phase and is complexed with labeled antibody (and where a monoclonal antibody is used, it is preferably specific for a given region of the protein). Then, a test compound could be assayed for its ability to disrupt the association of the protein/antibody complex.

In practice, microtiter plates, or any modernized iteration thereof, may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the test protein, polypeptide, peptide or fusion protein, or the test compound to anchor any complexes formed in solution, and a labeled antibody specific for the other component of the possible complex to detect anchored complexes.

Macromolecules that interact with a given regulatory or test protein are referred to, for purposes of this discussion, as "binding partners". Therefore, it is desirable to identify compounds that interfere with or disrupt the interaction with such binding partners which may be useful in regulating the gene activity.

The basic principle of the assay systems used to identify compounds that interfere with the interaction between the a protein and its binding partner or partners involves preparing a reaction mixture containing the test protein, polypeptide, peptide or fusion protein as described above, and the binding partner under conditions and for a time sufficient to allow the two to interact and bind, thus forming a complex. In order to test a compound for inhibitory activity, the reaction mixture is prepared in the presence and absence of the test compound. The test compound can be initially included in the reaction mixture, or may be added at a time subsequent to the addition of the test protein and its binding partner. Control reaction mixtures are incubated without the test compound or with a placebo. The formation of any complexes between the test protein and the binding partner is then detected. The formation of a complex in the control reaction, but not in the reaction mixture containing the test compound, indicates that the compound interferes with the interaction of the test protein and the binding partner.

The assay for compounds that interfere with protein binding can be conducted in a heterogeneous or homogeneous format. Heterogeneous assays involve anchoring either the test protein or the binding partner onto a solid phase and detecting complexes anchored on the solid phase at the end of the reaction. In homogeneous assays, the entire reaction is carried out in a liquid phase. The examples below describe similar assays which may be easily modified to screen for compounds which disrupt or enhance the interaction. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the test protein and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the test protein, or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the test protein or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the test protein and the interactive binding partner is prepared in which either protein is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt the binding interaction can be identified.

For example of a typical labeling procedure, a test protein or a peptide fragment, e.g., corresponding to the relevant binding domain, can be fused to a glutathione-S-transferase (GST) gene using a fusion vector, such as pGEX-5X-1, in such a manner that its binding activity is maintained in the resulting fusion protein. The interactive binding partner can be labeled with radioactive isotope, for example, by methods routinely practiced in the art. In a heterogeneous assay, e.g., the GST-fusion protein can be anchored to glutathione-agarose beads. The interactive binding partner can then be added in the presence or absence of the test compound in a manner that allows interaction and binding to occur. At the end of the reaction period, unbound material can be washed away. The interaction between the fusion product and the labeled interactive binding partner can be detected by measuring the amount of radioactivity that remains associated with the glutathione-agarose beads. The successful inhibition of binding by the test compound will result in a decrease in measured radioactivity.

Alternatively, the GST-fusion protein and the labeled interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of binding inhibition can be measured by determining the amount of radioactivity associated with the beads.

In another embodiment of the invention, these same techniques can be employed using peptide fragments that correspond to the binding domains of the test proteins, in place of the full length proteins. Any number of methods routinely practiced in the art can be used to identify and isolate the binding sites. These methods include, but are not limited to, mutagenesis of the gene encoding the protein and screening for disruption of binding in a co-immunoprecipitation assay. Sequence analysis of the gene encoding the protein will reveal the mutations that correspond to the region of the protein involved in interactive binding.

The invention encompasses cell-based and animal model-based assays for the identification of compounds exhibiting the ability to alter or correct phenotypes associated with the various genotypes identified and constructed using the present methods. Such cell-based assays can also be used as the standard to assay for purity and potency of the compounds, including recombinantly or synthetically produced proteins or compounds.

Cell-based systems can also be used to identify assess the amount of altered gene expression in a living cell. One tool of particular interest for such assays is green 10 fluorescent protein which is described, inter alia, in U.S. Pat. No. 5,625,048, herein incorporated by reference. Cells that may be used in such cellular assays include, but are not limited to, leukocytes, or cell lines derived from leukocytes, lymphocytes, stem cells, including embryonic stem cells, and the like. In addition, expression host cells (e.g., B95 cells, COS cells, CHO cells, OMK cells, fibroblasts, Sf9 cells) genetically engineered to express a functional proteins of interest and to respond to activation by the natural ligand, as measured by a chemical or phenotypic change, or induction of another host cell gene, can be used as an end point in the assay.

In utilizing such cell systems, cells may be exposed to a compound suspected of exhibiting an ability to affect target gene expression or activation, at a sufficient concentration and for a time sufficient to elicit such an effect in the exposed cells. After exposure, the cells can be assayed to measure alterations in the expression of the desired gene, e.g., by assaying cell lysates for the amount of relevant mRNA transcript (e.g., by Northern analysis), or by directly assaying the amount of a particular protein expressed in the cell. Using such methodology, compounds that regulate or modulate expression of the gene of interest are identified as valuable candidates for therapeutic development. Alternatively, the cells are examined to determine whether one or more cellular phenotypes have been altered to resemble a more normal or a more wild type phenotype, or a phenotype more likely to produce a lower incidence or response to a given stimulus.

In addition, animal-based systems, which may include, for example, mice, may be used to identify compounds having a given activity. For example, there are a number of model systems which comprise "knockdown" mice expressing reduced levels of various receptors. In addition, there are a number of mouse models of targeted overexpression of receptors.

Such animal models may be used as test systems for the identification of drugs, pharmaceuticals, therapies and interventions which may be effective in treating such disorders.

As an example, animals, such as transgeneic animals made using the claimed methods, can be exposed to a compound suspected of exhibiting an ability to interfere with the a given receptor, or regulatory cascade. The response of the animals to the compound may be monitored by assessing the extent of change, or even reversal, of the engineered phenotype. With regard to intervention, any treatments which reverse any aspect of a given phenotype in vivo should be considered as candidates for further development or potential use in humans. Dosages of test agents may be determined by deriving dose-response curves using methods well known in the art.

The present invention is further illustrated by the following examples, which are not intended to be limiting in any way whatsoever.

6.0. EXAMPLES

6.1. Btk Vector Construction

The promoter from the mouse phosphoglycerate kinase (AGK) gene was placed upstream from the first exon of the naturally occurring murine btk gene (nucleotides 40,043 to 40,250 of the murine btk gene). The first exon of the btk gene does not contain a translational start site and initiation codon marking the 51 region of the coding sequence; however, these features could be engineered into the exon if desired. The 3' end of the coding region of the first exon is marked by a splice donor sequence. Given that splice donor recognition sequences can extend into intronic sequence, 103 bases of intron DNA was retained after the end of the btk first exon. The PGKbtkSD cassette lacks a 3, polyadenylation signal. Accordingly, any transcript produced by the cassette cannot be properly processed, and therefore identified by 3' RACE, unless the transcript is spliced to a 3' exon that can be polyadenylated.

The above 3' gene trap cassette was place into a retroviral vector that incorporated a polyadenylation site 5' to the PGK promoter of the 3' gene trap cassette, the IREβggeo sequence (i.e., foreign mutagenic polynucleotide sequence) was placed 5' to the polyadenylation site, and a splice acceptor site was placed 5' to the IREβpgeo coding region. This vector also incorporates, in operable combination, a pair of recombinase recognition sites that flank the PGKbtkSD cassette (See FIG. 2). This vector typically requires that the target cell naturally express the trapped gene; however, this requirement can be overcome by adding a promoter that independently controls the expression of the selectable marker.

6.2. 3' Gene Trapping

The btk vector was introduced into the embryonic stem cells using standard techniques. In brief, supernatant from GP+E packaging cells was added to approximately $2 \times 10^6$ embryonic stem cells (at an input ratio of approximately 0.1 virus/target cell) for 16 hours and the cells were subsequently selected with G418 for 10 days. G418 resistant cells were subsequently isolated, grown up on 96-well plates and subjected to automated RNA isolation, reverse transcription, PCR and sequencing protocols to obtain the sequence tag.

RNA Isolation was carried out on DNA bind plates (Corning/costar) treated with 51-amino $(dT)_{42}$ (GenoSys Biotechnologies) in a 50 mM Sodium Phosphate buffer, pH 8.6, and allowed to sit at room temperature overnight.

Immediately prior to use the plates were rinsed three times with PBS and twice with TE. Cells were rinsed with PBS, lysed with a solution containing 100 mM Tris-HCl, 500 mM LiCl, 10 mM EDTA, 1% LiDS, and 5 mM DTT in DEPC water, and transferred to the DNA binding plate where the mRNA was captured. After a 15 minute incubation the RNA was washed twice with a solution containing 10 mM Tris-HCl, 150 mM LiCl, 1 mM EDTA, and 0.1% LiDS in DEPC water. The RNA was then rinsed three times with the same solution minus LiDS.

Elution buffer containing 2 mM EDTA in DEPC water was added and the plate was heated at 70° C. for five minutes. An RT premix containing 2× First Strand buffer, 100 mM Tris-HCl, pH 8.3, 150 mM KCl, 6 mM $MgCl_2$, 2 mM dNTPs, RNAGuard (1.5 units/reaction, Pharmacia), 20 mM DTT, QT primer (3 pmol/rxn, GenoSys Biotechnologies, sequence: 5'CCAGTGAGCAGAGTGAC-GAGG ACTCGAGCTCAAGCTTTTTTTTTTTTTTTTT 3', SEQ ID NO:1) and Superscript II enzyme (200 units/rxn, Life Technologies) was added. The plate was transferred to a thermal cycler for the RT reaction (37° C. for 5 min. 42° C. for 30 min. and 55° C. for 10 min).

6.2.1. PCR Product Generation

The cDNA was amplified using two rounds of PCR. The PCR premix contains: 1.1× MGBII buffer (74 mM Tris pH 8.8, 18.3 mM Ammonium Sulfate, 7.4 mM $MgCl_2$, 5.5 mM 2 ME, 0.011% Gelatin), 11.1% DMSO (Sigma), 1.67 mM dNTPS, Taq (5 units/rxn), water and primers. The sequences of the first round primers are: $P_o$ 5'AAGCCCGGTGCCTGACTAGCTAG3', SEQ ID NO:2 (BTK, 5'GAATATGTCTCCAGGTCCAGAG3', SEQ ID NO:3) and $Q_o$ 5'CCAGTGAGCAGAGTGACGAGGAC3', SEQ ID NO:4 (pmol/rxn). The sequences of the second round primers are $P_i$ 5'CTAGCTAGGGAGCTCGTC3', SEQ ID NO:5 (BTK, $_i$ 5'CCAGAGTCTTCAGAGATCAAGTC3', SEQ ID NO:6) and $Q_i$ 5'GAGGACTCGAGCTCAAGC3', SEQ ID NO:7 (50 pmol/rxn). The outer premix was added to an aliquot of cDNA and run for 17 cycles (95° C. for 1 min. 94° C. for 30 sec., 58° C. for 30 sec 65° C. for 3.5 min). An aliquot of this product was added to the inner premix and cycled at the same temperatures 40 times.

The nested 3' RACE products were purified in a 96-well microtiter plate format using a two-step protocol as follows. Twenty-five microliters of each PCR product was applied to a 0.25 ml bed of Sephacryl® S-300 (Pharmacia Biotech AB, Uppsala, Sweden) that was previously equilibrated with STE buffer (150 mM NaCl, 10 MM Tris-HCL, 1 mM EDTA, pH 8.0). The products were recovered by centrifugation at 1200 × g for 5 minutes. This step removes unincorporated nucleotides, oligonucleotides, and primer-dimers. Next, the products were applied to a 0.25 ml bed of Sephadex® G-50 (DNA Grade, Pharmacia Biotech AB) that was equilibrated in MilliQ $H_2O$, and recovered by centrifugation as described earlier. Purified PCR products were quantified by fluorescence using PicoGreen (Molecular Probes, Inc., Eugene Oreg.) as per the manufacturer's instructions.

Dye terminator cycle sequencing reaction with Ampli-Taq® FS DNA polymerase (Perkin Elmer Applied Biosystems, Foster City, Calif.) were carried out using 7 pmoles of primer (Oligonucleotide OBS; 5'CTGTAAAACGACGGCCAGTC3', SEQ ID NO:8) and approximately 30–120 ng of 3' RACE product. The cycling profile was 35 cycles of 95° C. for 10 sec. 55° C. for 30 sec, and 60° C. for 2 min. Unincorporated dye terminators were removed from the completed sequencing reactions using G-50 columns as described earlier. The reactions were dried under vacuum, resuspending in loading buffer, and electrophoresed through a 6% Long Ranger acrylamide gel (FMC BioProducts, Rockland, Me.) on an ABI Prism® 377 with XL upgrade as per the manufacturer's instructions.

The automated 96-well format was used to obtain sequence, and data was obtained from 70% of the colonies. Upon examination, the sequence from the first exon of btk was identified followed by the btk splice junction. The splice junction was followed by unique sequences from each separate gene trap event. These sequences averaged 500 bp in length and were of high quality often containing long open reading frames. In addition 80% of these sequences can be matched using blast searches to sequences found in the Genbank database indicating that transcribed exonic sequences were identified. These sequence tags are of significantly better length and quality than those produced by previous gene trap designs. The new tags are improved in both length and quality and the fact that 80% of the tags match Genbank sequences suggests that they efficiently trap genes.

These data indicate that the splicing machinery is better able to recognize an exon type sequence present adjacent to or relatively close to a promoter when splicing into downstream exons. These data also indicate that the majority of G418 resistant colonies can be identified using sequence tags. DNA sequence data had already been obtained that represents approximately 7,000 different genes trapped by a vector incorporating a PGKpuroSD 3' gene trap cassette in conjunction with puro selection. Given that it has already been established that such vectors typically produce 13 fold more G418 resistant colonies than puro colonies, vectors incorporating the presently described 3' gene trap cassette have a very large target size, probably well over 70,000 genes. This target can be further increased by using SAneopA rather than the SAβgeo fusion to increase the sensitivity of antibiotic selection, and any other selectable, or otherwise identifiable, marker could be used in the 5' gene trap cassette instead of neo. The use of IRESneo increased the number of G418 resistant colonies to over 15× the number of puro resistant colonies demonstrating its increased sensitivity. Other potential 5' trapping markers include, but are not limited to, antibiotic resistance genes (e.g., a-lactamase), calorimetric marker genes, genes encoding recombinase activity (e.g., flp or cre, etc.), enzymes, fluorescent marker genes (e.g., genes encoding activities that directly or indirectly mediate cellular fluorescence) such as the gene encoding green fluorescent protein, and assays for detecting the same, which are described, inter alia, in U.S. Pat. No. 5,625,048, herein incorporated by reference.

Typically, the more sensitive the selectable marker, the greater the number of target genes that can be trapped. The ability to use the btk first exon to obtain sequence tags from the 3' exons of the G418 resistant colonies produced approximately 13 fold more mutated cells than could be mutated and rapidly sequenced using previous vectors, and thus represents a significant improvement in gene trapping technology.

Given the above results, it is clear that the surprising and unexpected properties that resulted in an order of magnitude improvement over any previously reported 3' gene trap cassettes were only realized by departing from our established selectable marker paradigm for gene trapping.

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of animal genetics and molecular biology or related fields are intended to be within the scope of the following claims.

What is claimed is:

1. A genetically engineered vector comprising:
   a) a 5' gene trap cassette comprising in operable combination:
      1) a splice acceptor;
      2) a first exon sequence located 3' to said splice acceptor, said first exon encoding a marker enabling the identification of a cell expressing said exon; and
      3) a polyadenylation sequence defining the 3' end of said first exon;
   b) a 3' gene trap cassette located 3' to said polyadenylation sequence comprising in operable combination:
      1) a first promoter;
      2) a second exon sequence located 3' from and expressed by said promoter, said second exon being derived from a naturally occuring eukaryotic gene, said second exon not encoding an activity conferring antibiotic resistance and said second exon not being a reporter gene;
      3) a splice donor sequence defining the 3' region of the exon said splice donor sequence being derived from a naturally occuring eukaryotic gene; and
   wherein said vector docs not encode a promoter mediating the expression of said first exon, and wherein said vector does not encode a sequence that mediates the polyadenylation of an mRNA transcript encoded by said second exon sequence and expressed by said first promoter.

2. The vector according to claim 1 wherein said first exon additionally encodes an internal ribosome entry site operatively positioned between said splice acceptor and the initiation codon of said first exon.

3. The vector of claim 1 wherein said first exon encodes a marker drawn from the group consisting of: a marker conferring antibiotic resistance; a marker conferring antibiotic sensitivity; an enzymatic marker: a recombinase, and a fluorescently detectable marker.

4. The vector of claim 3 wherein said marker encodes neomycin resistance.

5. A genetically engineered vector comprising:
   a) a marker gene expressed by a vector encoded promoter; and
   b) a 3' gene trap cassette comprising in operable combination:
      1) a second promoter;
      2) an exon sequence located 3' from and expressed by said second promoters said exon being derived from a naturally occuring, eukaryotic gene, said second exon not encoding an activity conferring antibiotic resistance and said exon not being a reporter gene;
      3) a splice donor sequence defining the 3' region of the exon, said splice donor sequence being derived from a naturally occuring eukaryotic acne; and
   wherein said vector does not encode a sequence that mediates the polyadenylation of an mRNA transcript encoded by said exon sequence.

6. A genetically engineered retroviral vector comprising:
   (a) a first retroviral LTR sequence;
   (b) a promoter operative in eukaryotic cells;
   (c) an exon sequence located 3' from and expressed by said promoter, said exon being derived from a naturally occuring eukaryotic gene, said second exon not encoding an activity conferring antibiotic resistance and said exon not being a reporter gene;
   (d) a splice donor sequence defining the 3' region of the exon said splice donor sequence being derived from a naturally occuring eukaryotic gene; and (e) a second retroviral LTR sequence;

wherein said promoter, exon and splice donor are present in the vector in between said first and second LTR sequence and in an opposite orientation to said first and second retroviral LTR sequences and wherein said vector does not incorporate a sequence that mediates the polyadenylation of an mRNA transcript expressed by said promoter of element (b) and encoded by said exon of element (c).

7. A method of gene trapping comprising introducing a vector according to any one of claims 1, 2 and 3 through 6 into an isolated eukaryotic target cell.

8. The method of claim 7 wherein said introducing of said vector into said eukaryotic target cell is carried out by a method drawn from the group consisting of electroporation, viral infection, retrotransposition, microinjection, and transfection.

9. The method of claim 8 wherein said eukaryotic cell is a mammalian cell.

10. The method of claim 9 wherein said mammalian cell is a murine embryonic stem cell.

11. A method of generating a library of isolated, nonspecifically mutated eukaryotic cells comprising introducing a vector according to any one of claims 1, 5 or 6 into eukaryotic cells to produce a collection of isolated, nonspecifically mutated eukaryotic cells.

12. A method to activate the expression of a naturally occurring gene in an isolated cell comprising introducing a vector according to any one of claims 1, 5 or 6 into said cell.

13. The method of claim 12 wherein said cell is a mammalian cell.

14. The method of claim 13 wherein said mammalian cell is a human cell.

15. A method to alter the expression of a gene in an isolated eukaryotic cell comprising introducing a 3' gene trap cassette vector into said cell, said 3' gene trap cassette comprising in operable combination:

1) a promoter;
2) an exon sequence located 3' from and expressed by said promoter, said exon being derived from a naturally occuring eukaryoric one said exon not encoding an activity conferring antibiotic resistance and said exon not being a reporter gene; and
3) a splice donor sequence defining the 3' region of said exon said slice donor sequence being derived from a naturally occuring eukaryotic gene;

wherein said cassette is non-homologously incorporated into the genome of an eukaryotic target cell and said splice donor sequence of the transcript encoded by said exon is spliced to a splice acceptor sequence of said cellularly encoded gene.

16. The method of claim 15 wherein said non-homologously incorporated cassette is present in a retroviral vector that has randomly integrated into the genome of the eukaryotic target cell.

17. The method of claim 16 wherein said eukaryotic target cell is an animal cell.

18. The method of claim 17 wherein said animal cell is a mammalian cell.

19. The method of claim 18 wherein said mammalian cell is a human cell.

20. The method of claim 18 wherein said mammalian cell is a rodent cell.

21. The method of claim 20 wherein said rodent cell is a mouse cell.

* * * * *

UNITED STATES PATENT AND TRADEMARK OFFICE
CERTIFICATE OF CORRECTION

PATENT NO. : 6,080,576

DATED: June 27, 2000

INVENTORS: Brian Zambrowicz, Glenn Friedrich, and Arthur T. Sands

It is hereby certified that errors appear in the above-identified patent and that said Letters Patent is hereby corrected as shown below:

In the Claims:

In claim 1, line 20, insert --,-- after the word "exon"; and in line 22, replace "docs" with --does-- after the word "vector".

In claim 3, line 4, replace ":" with --;-- after the word "marker".

In claim 5, line 8, replace "promoters" with --promoter,-- after the word "second"; in line 9, delete "," after the word "occurring"; and in line 14, replace "acne" with --gene-- after the word "eukaryotic".

In claim 6, line 6, delete "second" after the word "said"; and in line 10, insert --,-- after the word "exon".

UNITED STATES PATENT AND TRADEMARK OFFICE
CERTIFICATE OF CORRECTION

PATENT NO.: 6,080,576

DATED: June 27, 2000

INVENTORS: Brian Zambrowicz, Glenn Friedrich, and Arthur T. Sands

It is certified that error appears in the above-identified patent and that said Letters Patent is hereby corrected as shown below:

In claim 15, line 8, replace "eukaryoric one" with --eukaryotic gene-- after the word "occuring"; in line 12 insert --,-- after the "exon"; and in line 15, insert --isolated-- before the word "eukaryotic".

Signed and Sealed this

Twenty-second Day of May, 2001

*Attest:*

NICHOLAS P. GODICI

*Attesting Officer*   Acting Director of the United States Patent and Trademark Office

```
                            SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
         (A) LENGTH: 52 base pairs
         (B) TYPE: nucleic acid
         (C) STRANDEDNESS: single
         (D) TOPOLOGY: linear (xi) SEQUENCE DESCRIPTION: SEQ ID NO:1:

CCAGTGAGCA GAGTGACGAG GACTCGAGCT CAAGCTTTTT TTTTTTTTTT TT            52

(2) INFORMATION FOR SEQ ID NO:2:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:2:

AAGCCCGGTG CCTGACTAGC TAG                                           23

(2) INFORMATION FOR SEQ ID NO:3:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (xi) SEQUENCE DESCRIPTION: SEQ ID NO:3:

GAATATGTCT CCAGGTCCAG AG                                            22

(2) INFORMATION FOR SEQ ID NO:4:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (xi) SEQUENCE DESCRIPTION: SEQ ID NO:4:

CCAGTGAGCA GAGTGACGAG GAC                                           23

(2) INFORMATION FOR SEQ ID NO:5:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO:5:

CTAGCTAGGG AGCTCGTC                                                 18
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

CCAGAGTCTT CAGAGATCAA GTC                                               23

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

GAGGACTCGA GCTCAAGC                                                     18

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

CTGTAAAACG ACGGCCAGTC                                                   20